(12) United States Patent
Abedin et al.

(10) Patent No.: US 9,244,226 B2
(45) Date of Patent: Jan. 26, 2016

(54) TERMINATION OF OPTICAL FIBER WITH LOW BACKREFLECTION

(71) Applicant: OFS Fitel, LLC, Norcross, GA (US)

(72) Inventors: Kazi S Abedin, Basking Ridge, NJ (US); David J Digiovanni, Mountain Lakes, NJ (US); Paul S Westbrook, Bridgewater, NJ (US)

(73) Assignee: OFS FITEL, LLC, Norcross, GA (US)

( * ) Notice: Subject to any disclaimer, the term of this patent is extended or adjusted under 35 U.S.C. 154(b) by 14 days.

(21) Appl. No.: 14/169,419

(22) Filed: Jan. 31, 2014

(65) Prior Publication Data

US 2015/0219851 A1    Aug. 6, 2015

(51) Int. Cl.
| | |
|---|---|
| *G02B 6/00* | (2006.01) |
| *G02B 6/26* | (2006.01) |
| *G01D 5/353* | (2006.01) |
| *G02B 6/24* | (2006.01) |
| *A61B 18/22* | (2006.01) |
| *G02B 6/42* | (2006.01) |

(52) U.S. Cl.
CPC ............ *G02B 6/262* (2013.01); *G01D 5/35316* (2013.01); *G01D 5/35383* (2013.01); *G02B 6/241* (2013.01); *A61B 2018/2272* (2013.01); *G02B 6/00* (2013.01); *G02B 6/4206* (2013.01); *G02B 6/4214* (2013.01)

(58) Field of Classification Search
CPC ............. A61B 1/07; A61B 2018/2272; G02B 6/3624; G02B 6/4214; G02B 6/262; G02B 6/00; G02B 6/4206
See application file for complete search history.

(56) References Cited

U.S. PATENT DOCUMENTS

| | | | | |
|---|---|---|---|---|
| 5,953,477 A | * | 9/1999 | Wach et al. | 385/115 |
| 2006/0137403 A1 | * | 6/2006 | Barr et al. | 65/377 |
| 2008/0013900 A1 | * | 1/2008 | Harris | 385/117 |
| 2009/0175576 A1 | * | 7/2009 | Tang | 385/31 |
| 2010/0021109 A1 | * | 1/2010 | Ohtsu et al. | 385/31 |
| 2011/0091181 A1 | * | 4/2011 | DeMeritt et al. | 385/140 |
| 2011/0255828 A1 | * | 10/2011 | Sudarshanam | 385/31 |
| 2013/0331689 A1 | * | 12/2013 | Le et al. | 600/425 |

* cited by examiner

*Primary Examiner* — Eric Wong
*Assistant Examiner* — Mary A El Shammaa
(74) *Attorney, Agent, or Firm* — Jacobs + Kim LLP

(57) ABSTRACT

A technique is described for terminating an optical fiber with low backreflection. At a selected end of the optical fiber segment, an endface is formed at a selected angle relative to the fiber axis. A suitable material is deposited onto the angled endface to form an angled reflective surface. The angled reflective surface is configured such that light propagating along the waveguide to the selected end of the optical fiber segment is reflected back into the optical fiber segment at an angle that prevents coupling of the reflected light into the fiber core. The reflected light is dissipated along the length of the fiber segment.

21 Claims, 9 Drawing Sheets

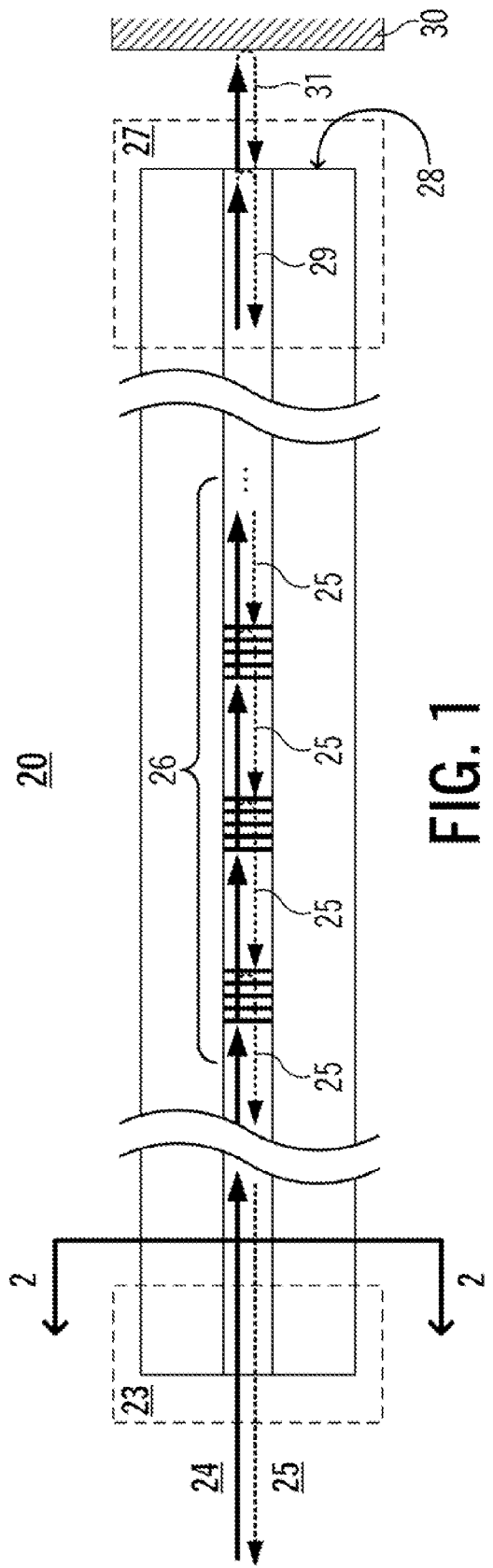
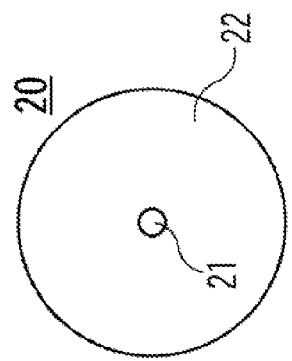
FIG. 1
(PRIOR ART)
FIG. 2
(PRIOR ART)

TERMINATION OF OPTICAL FIBER WITH LOW BACKREFLECTION

BACKGROUND OF THE INVENTION

1. Field of the Invention

The present invention relates generally to the field of fiber optics, and in particular to systems and techniques for terminating an optical fiber with low backreflection.

2. Background Art

In a fiber-optic sensor, a reference light is launched into a sensor fiber and the resulting backreflected light is detected and analyzed. A fiber-optic sensor can be used, for example, to detect changes in shape and/or position based on the measurement of the amplitude/phase of distributed backreflection along the length of the sensor fiber. In a shape/position sensor, and in other sensor applications, it is of utmost importance to suppress backreflection coming from the tip of the sensor fiber. A strong reflection from the tip can adversely saturate the detector used to detect distributed backreflection, and consequently impair the accuracy and resolution of the shape/position sensing.

While conventional methods for terminating a sensor fiber are capable of reducing backreflection from the fiber tip, the sensor performance can become highly sensitive to touch or to backreflection or backscattering from nearby objects. In a shape-sensing application, a sensor fiber is typically deployed within a tightly confined region. Light emitted from the tip of the sensor fiber can be reflected by the surfaces of the confined region back into the sensor fiber and coupled into the fiber core. Furthermore, the properties of the medium surrounding the tip can alter the behavior of light at the tip, increasing reflectivity, for example.

One way to overcome this problem is to attach a backreflection-suppression element, such as a light-absorbing glass rod or fiber, to the tip of the sensor fiber. Light emitted from the sensor fiber tip propagates through the absorbing structure, and is attenuated by such an extent that reflection from nearby objects becomes insignificant. However, the addition of the light-absorbing structure poses a number of problems.

First, the attachment of a light-absorbing structure to the fiber tip affects the positional accuracy of the sensor because of the lack of a sensing element (e.g., Bragg grating) in the appended structure. The light-absorbing structure has to have a length of at least a few millimeters in order to provide sufficient suppression of light emitted from the fiber tip. Thus, the positional accuracy of the sensor tip is limited by the length of the added structure.

Second, the light-absorbing structure typically has a refractive index that is different from that of silica glass fiber. Therefore, in order to suppress backreflection from the interface between the sensor fiber and the light-absorbing structure, a special splicing technique is needed, involving the use of a thermal diffusion technique to achieve index matching. The special splicing technique calls for individual processing of each fiber sensor, thus making batch processing difficult. Further, the strength of the sensor tip is compromised. The presence of the spliced component means that the sensor tip is increasingly prone to breakage/fracture as it is passed through tight bends.

SUMMARY OF INVENTION

Aspects of the invention are directed to structures and techniques for terminating an optical fiber with low backreflection. The described structures and techniques satisfy a number of criteria, including: low reflectivity; insensitivity to touch or nearness of external surfaces or objects; compactness; no additional attachment that can otherwise affect the positional accuracy; no compromise of mechanical strength; and the ability to be manufactured in a scalable manner.

In one practice of the invention, the tip of an optical fiber segment is provided with an endface that is angled relative to the fiber axis. A suitable material is deposited onto the angled endface to form an angled reflective surface. The reflective surface is configured such that light reaching the fiber tip is reflected back into the optical fiber segment at an angle that prevents coupling of the reflected light into the fiber core, and that allows the backreflected light to dissipate.

Further aspects of the invention are directed to the selection of a suitable angle for the reflective surface, and to structures and techniques for terminating a multicore sensor fiber.

BRIEF DESCRIPTION OF THE DRAWINGS

FIG. 1 shows a cross-section diagram of an exemplary single-core sensor fiber.

FIG. 2 shows a cross-section diagram of the fiber shown in FIG. 1 through the plane 2-2.

DETAILED DESCRIPTION

Figure 3:
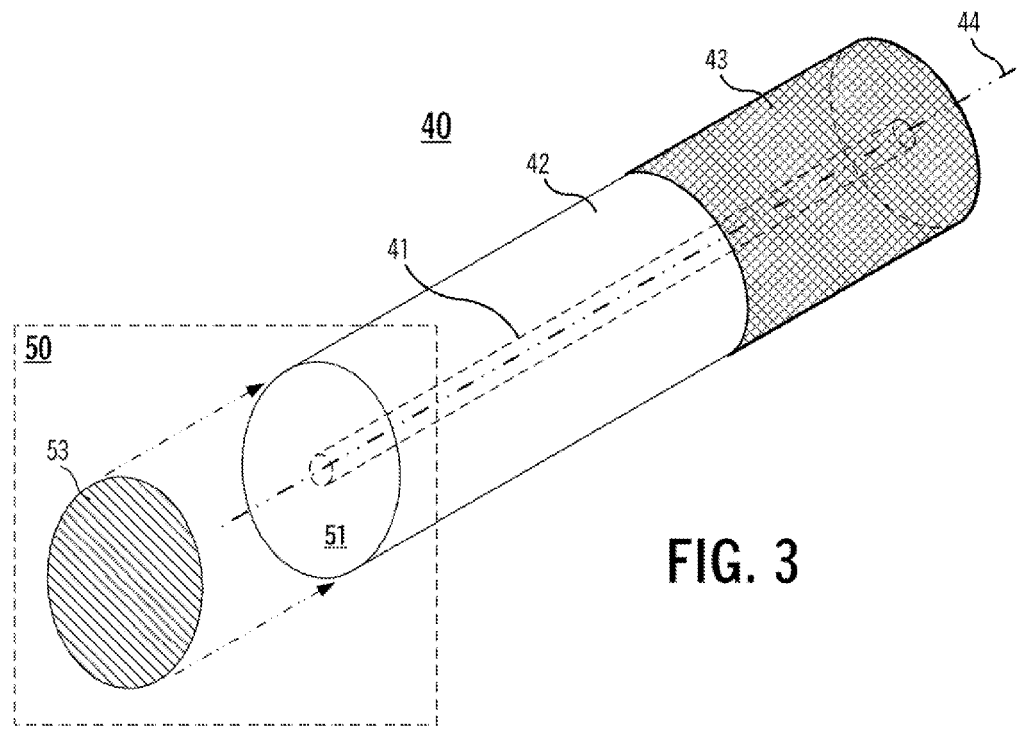
FIG. 3 shows an isometric view of the tip of an single-core sensor fiber that has been provided with a low-backreflection termination structure according to an aspect of the invention.

Aspects of the present invention are directed to structures and techniques for terminating a sensor fiber so as to suppress backreflection from the fiber tip. A termination structure in accordance with the aspects of the invention described herein is extremely compact, having a diameter that is the same as the sensor fiber and a length that is shorter than half the fiber diameter. In addition, the described termination structure is insensitive to proximity to, or contact with, external objects; has the same mechanical strength as the sensor fiber; and is highly suitable for volume production.

FIG. 1 shows a simplified, generic cross-section diagram of a single-core sensor fiber 20, and FIG. 2 shows a cross-section diagram through the plane 2-2. Sensor fiber 20 comprises a core 21 and cladding 22 that provide a light waveguide along the length of the fiber 20.

A sensing apparatus (not shown) is connected to the fiber's tail end 23. A reference light input 24 is launched into the sensor fiber 20, and the backreflected light 25 is detected and analyzed. In the present example, backreflection is provided by an array of fiber Bragg gratings 26. Backreflection may also be provided by other means, such as Rayleigh scattering.

In sensor fiber 20, a portion of the reference light input is reflected by each grating in array 26 back towards the sensor apparatus at the fiber's tail end 23. Changes in a physical quantity to be monitored result in corresponding changes in the respective wavelength responses of each individual grating. Thus, sensor fiber 20 provides distributed sensing over the length of the grating array 26.

Further, in sensor fiber 20, a portion of the reference light 24 propagates to the fiber tip 27 and is reflected by the fiber tip endface 28, resulting in an undesirable backreflection 29 from the fiber tip 27. Additionally, some of the reference light 24 may be emitted from the endface 28 and may be reflected by an external object 30, resulting in an additional undesirable backreflection 31 that reenters the fiber tip 27 through endface 28. Materials in contact with endface 28 may alter the reflective properties of the endface, inducing variability to the amount of backreflection 29.

As discussed above, a strong backreflection from the sensor fiber tip can adversely saturate the detector used to detect distributed backreflection, and consequently impair sensing accuracy and resolution. Depending on whether a sensor employs fiber Bragg gratings or Rayleigh scattering as a means of distributed backreflection, the backreflection from the sensor tip needs to be suppressed such that it does not exceed a specified maximum level, ranging from −40 dB to −80 dB. As discussed below, the structures and techniques described herein are capable of reducing backreflection to these levels, and even further.

Figure 4:
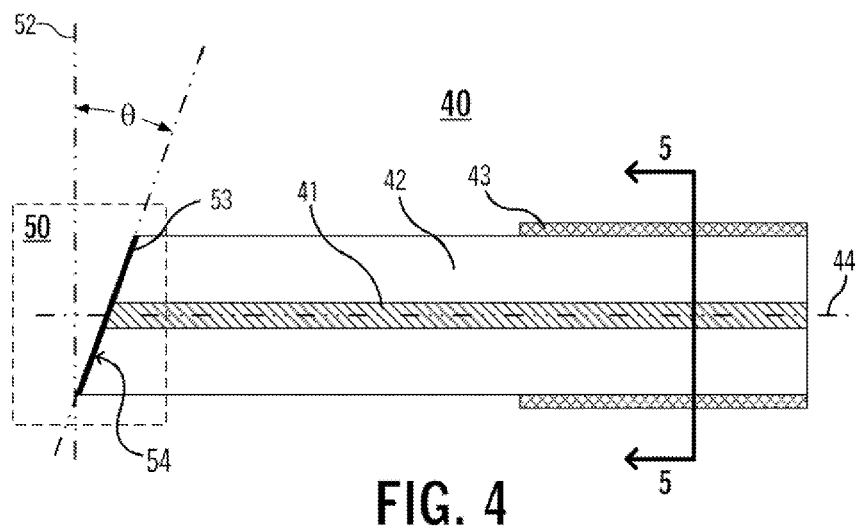
FIG. 4 shows a side cross section of the sensor fiber tip and termination structure shown in FIG. 3.
Figure 5:
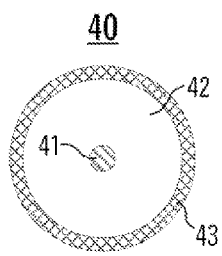
FIG. 5 shows a cross section of the sensor fiber tip shown in FIGS. 3 and 4 through the plane 5-5.

FIG. 3 shows an isometric view (not drawn to scale) of the tip of an exemplary single-core sensor fiber 40 that incorporates a low-backreflection termination structure 50 according to an aspect of the invention. FIG. 4 shows a side cross section of fiber segment 40, and FIG. 5 shows a cross section of fiber segment 40 through the plane 5-5. (It will be appreciated that the present discussion of single-core sensor fiber 20 also applies to a sensor fiber having a plurality of cores.)

Optical fiber segment 40 comprises a core 41, cladding 42, and outer coating 43, and is configured to provide a waveguide for the transmission of light along the fiber axis 44. A selected end of the optical fiber segment (i.e., the fiber tip) comprises an endface 51 at a selected angle $\theta$ relative to a plane 52 perpendicular to the fiber axis 44. The angled endface 51 has deposited thereon a suitable material 53, so as to form an angled reflective surface 54.

In the depicted exemplary practice, endface 51 is flat. It will be appreciated that a number of different geometric configurations may be used to achieve the suppression of backreflected light described herein. For example, as discussed below, endface 51 may have a convex shape.

Figure 6:
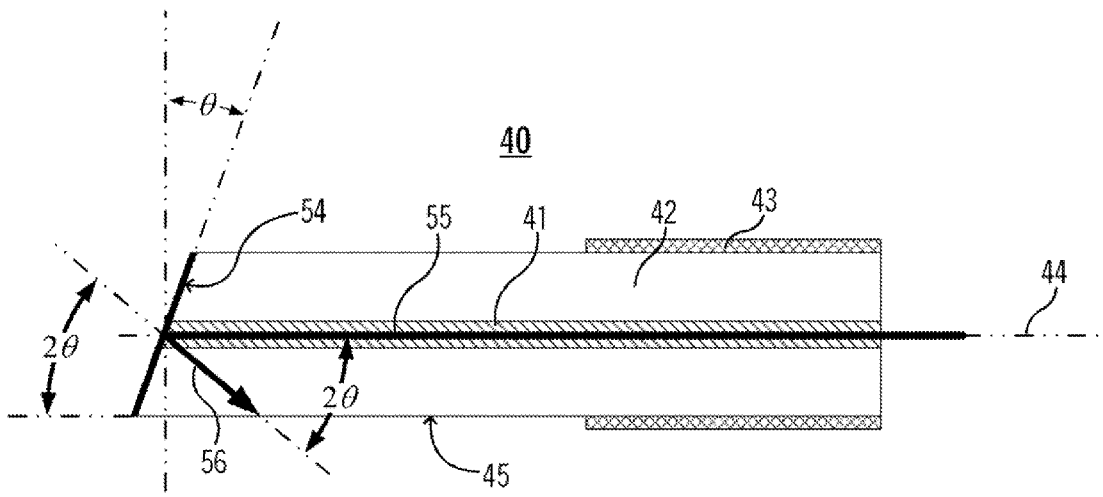
FIGS. 6 and 7 are cross section diagrams illustrating the backreflection of a reference light by the termination structure shown in FIGS. 3 and 4.
Figure 7:
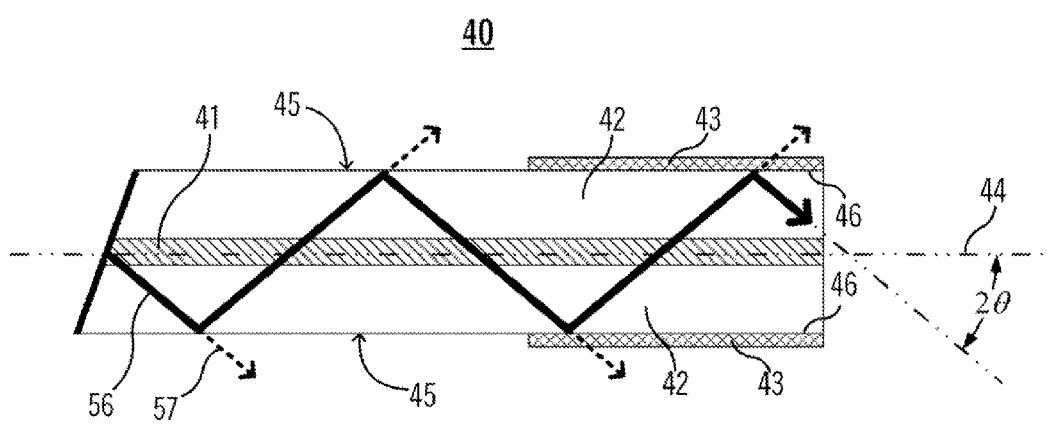

FIGS. 6 and 7 are cross section diagrams illustrating the operation of the invention. In FIG. 6, a portion of a reference light 55 propagating along the fiber axis 43 strikes the reflective surface 54. The backreflected light 56 is reflected back into the body of the fiber 40 at an angle of $2\theta$ relative to the fiber axis. Angle $2\theta$ is configured to be large enough to prevent coupling of the backreflected light 56 into the fiber core 41. The selection of a suitable value for $\theta$ is discussed below.

FIG. 7 illustrates the propagation of the backreflected light 56 back through fiber segment 40. After being reflected by reflective surface 54, the backreflected light propagates towards the fiber wall 45 with an angle of incidence of ~2θ. A number of things can happen to backreflected light 56: (a) it can be absorbed into the coating 43; (b) it can be reflected back into the cladding 42; or (c) it can leak out of the fiber through the coating or cladding (if exposed). Light leaking out of the exposed portion of the cladding 57 at the fiber tip leaks into the environment. Away from the fiber tip, light leaking out of the cladding 57 leaks into the coating 43.

Because of its angle $2\theta$ relative to the fiber axis 44, virtually none of the backreflected light 56 will be coupled into the fiber core 41. As it propagates back down the length of fiber 40, the backreflected light will continue to be reflected, absorbed, or subject to leakage, thus resulting in suppression of substantially all of the backreflected light before it reaches the fiber's input end.

FIGS. 8A-8D are a series of diagrams illustrating an exemplary technique for constructing the low-backreflection termination structure 50 depicted in FIGS. 3 and 4.

Figure 8A:
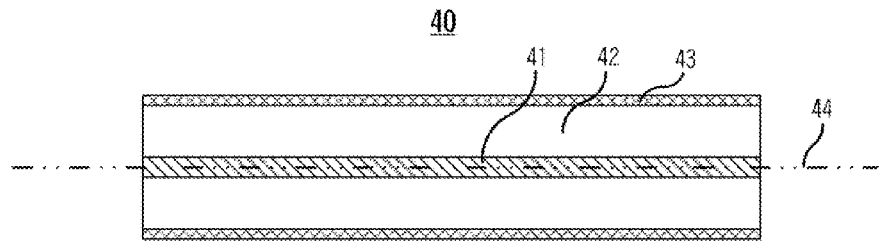
FIGS. 8A-8D are a series of diagrams illustrating an exemplary technique for constructing the low-backreflection termination structure shown in FIGS. 3 and 4.
Figure 8B:
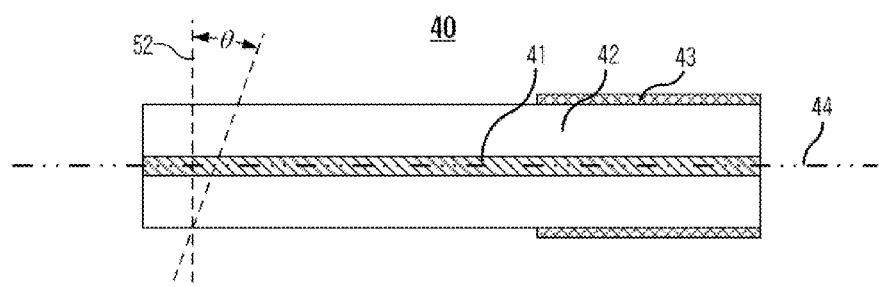

FIG. 8A shows a cross section diagram of the tip of a fiber segment 40, prior to termination. The first step, illustrated in FIG. 8B, is to strip off the outer coating 43 and to form a fiber endface 51 at a prescribed angle $\theta$, relative to a plane 52 perpendicular to the fiber axis 44. Stripping of the coating may be omitted. The angled endface 51 can be formed in different ways. For example, a flat-polishing technique may be used. Alternatively, the angled endface 51 can be formed using a cleaving technique employing a $CO_2$ laser or other suitable instrument.

Figure 8C:
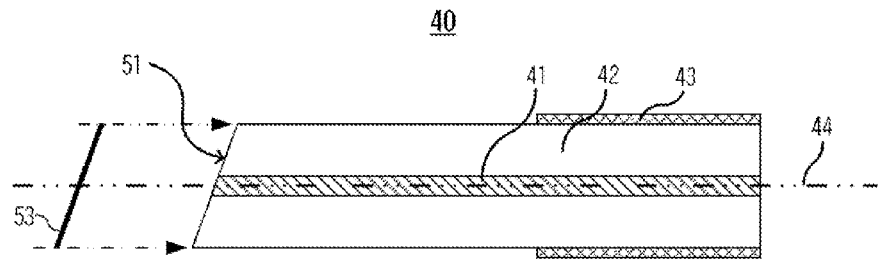
Figure 8D:
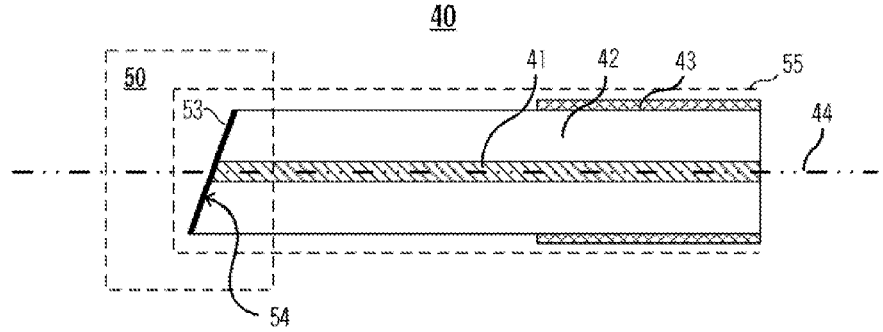

In the next step, illustrated in FIG. 8C, the polished surface 51 is coated with a suitable material 53 so as to form a highly reflective surface 54 (FIG. 8D). (It is noted that a suitable material may not be reflective by itself and may become so when deposited onto the fiber endface.) According to a further aspect of the invention, after the material 53 has been applied to the endface 51, the exposed fiber and tip can be further protected by covering them with a suitable polymeric coating 55 (show in broken lines).

According to an aspect of the invention, a suitable deposition technique is used to coat the polished endface 51 with a suitable material 53, such as indium, gold, or chromium, or a suitable combination thereof, having a suitable adherence to silica and providing high reflectivity (i.e., ~100%). It would also be possible to use multilayer coatings of dielectric materials such as $TiO_2$ and $ZrO_2$, or other suitable material.

The thickness of the deposited material is sufficient to achieve the desired level of reflectivity. For a typical sensor application, a suitable level of reflectivity can be achieved using a coating having a thickness of approximately 10 μm, or less. It is important that the smoothness of the angled endface 51 and highly reflecting coating 53 deposited on it be of sufficiently high quality so as to suppress scattering of light due to surface roughness, which otherwise can increase the light guided by the core.

The low-backreflection termination structure described herein has a number of advantages compared with other termination structures.

First, the termination structure is highly compact. Its diameter (projected into a plane perpendicular to the fiber axis) is equal to that of the sensor fiber. Where $\theta<45°$, the overall length of the termination structure is less than half the fiber diameter.

Second, the use of a highly reflective coating ensures that no forward-propagating light exits from the tip of the sensor fiber. Thus, the termination structure is insensitive to physical contact with, or proximity to, external objects.

Third, the described termination structure allows sensing to be performed substantially all the way into the termination structure. For example, in a grating-based sensor, gratings can be inscribed into the sensor fiber substantially all the way up to the polished endface.

Also, since the termination process does not involve heating of the tips of the sensor fiber to a high temperature, such as those used in splicing, diffusion or mechanical deformation, it does not affect the optical or mechanical properties of the sensor fiber cores or gratings inscribed into the cores.

In addition, due to the nature of the polishing and coating process, multiple sensor fibers can be processed in a batch to fabricate a respective termination structure for each sensor fiber, thereby reducing the manufacturing cost and processing time.

It is further noted that, depending on the needs of a particular application, it may be possible to achieve a suitably low level of backreflection using an opaque, non-reflective material deposited onto the angled endface 51.

Selection of Angle of Reflective Surface

There is now described a technique according to an aspect of the invention for calculating a suitable polishing angle θ. It is noted that a suitable polishing angle θ can also be arrived at empirically, i.e., through a trial-and-error approach, or through a combination of analytical and empirical approaches.

When an optical fiber is polished or cleaved at angle θ (relative to a plane perpendicular to the fiber axis) and coated with a suitable material so as to form a reflective surface, light propagating along the fiber axis is reflected at an angle of 2θ (relative to the fiber axis). The fraction of the reflected light that gets coupled into the core, can be obtained from the following equation (1):

$$R = \frac{2}{1+\cos^2(2\theta)} \exp\left(-\frac{2\pi^2 n^2 \omega^2}{\lambda^2} \frac{2\sin^2(2\theta)}{1+\cos^2(2\theta)}\right) \quad (1)$$

where

θ is the endface angle relative to the fiber axis;
n is the refractive index of the core;
ω is the spot size;
λ is the wavelength of light.

Figure 9:
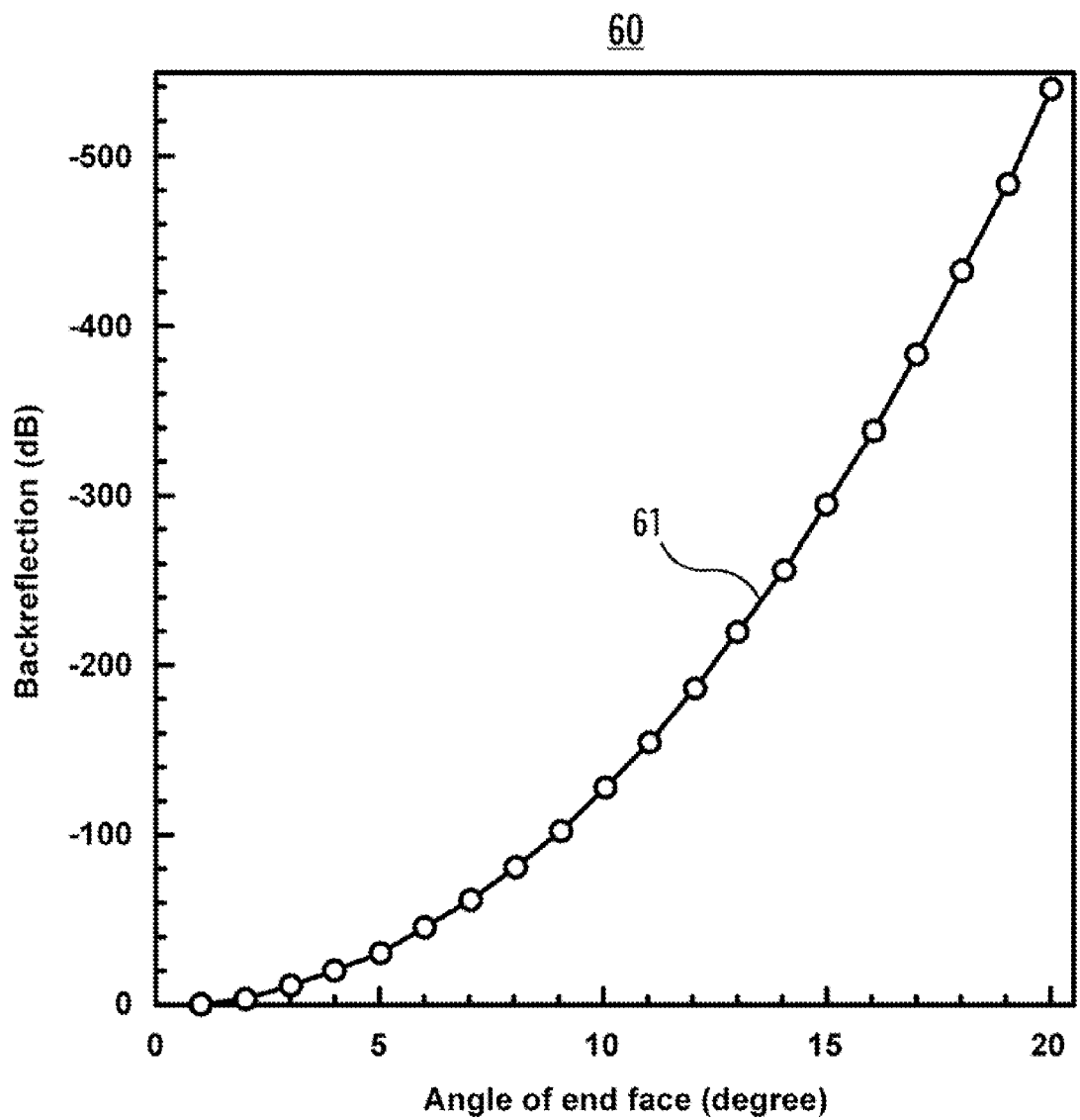
FIG. 9 shows a graph illustrating the relationship between backreflection (in dB) and endface angle θ for an exemplary optical fiber.

FIG. 9 shows a graph 60 illustrating the relationship between backreflection (in dB) and endface angle θ, for an optical fiber having the following parameters:

n=1.467;
λ=1.55 μm;
ω=5.2 μm.

Plot 61 shows that even if a coated endface has a reflectivity approaching 100%, the amount of backreflected light that is actually guided by the core can be very small (i.e., many tens of dBs lower than the incident light), depending upon the endface angle. Depending upon the requirements of a given application, endface angles ranging from a few degrees to a few tens of degrees will be sufficient to suppress backreflection adequately.

Using a metal coating, such as gold, on a silica optical fiber has the advantage that light can be efficiently reflected without causing light scattering. Backreflection can be readily suppressed below −20 dB using a coating having a thickness of 1 μm or greater. In a sensor fiber with double-pass evanescent field absorption, backreflection can be suppressed below −40 dB. Even if reflection from an external surface near the tip causes a backreflection of 1% (−20 dB), it is the backreflected light that may be coupled into the core should be −60 dB or lower.

It is important that light reflected into the cladding from the reflective angled endface remains uncoupled from the core, and decays as it propagates along the fiber. If the fiber coating 43 has an index higher than that of the cladding 42, light reaching the cladding-coating interface 46 can escape from the cladding. However, if the refractive index of the coating is lower than that of the cladding, it is important that the angle of incidence of the backreflected light on the fiber coating (i.e., 2θ) be larger than the critical angle of the cladding-coating interface. Thus, the following condition must be met:

$$2\theta > \sin^{-1}\left(\frac{NA_{cladding}}{n_{cladding}}\right) \quad (2)$$

Currently polymers used for low-index coating can provide a numerical aperture (NA) as high as 0.45. Assuming that the cladding has a refractive index of 1.47, the minimum angle θ required is 8.9°. Therefore, even if the coating has an index lower than that of the glass cladding, light can always escape the cladding, so long as the endface angle is greater than θ indicated in equation (2).

Termination of a Multicore Sensor Fiber

Figure 10:
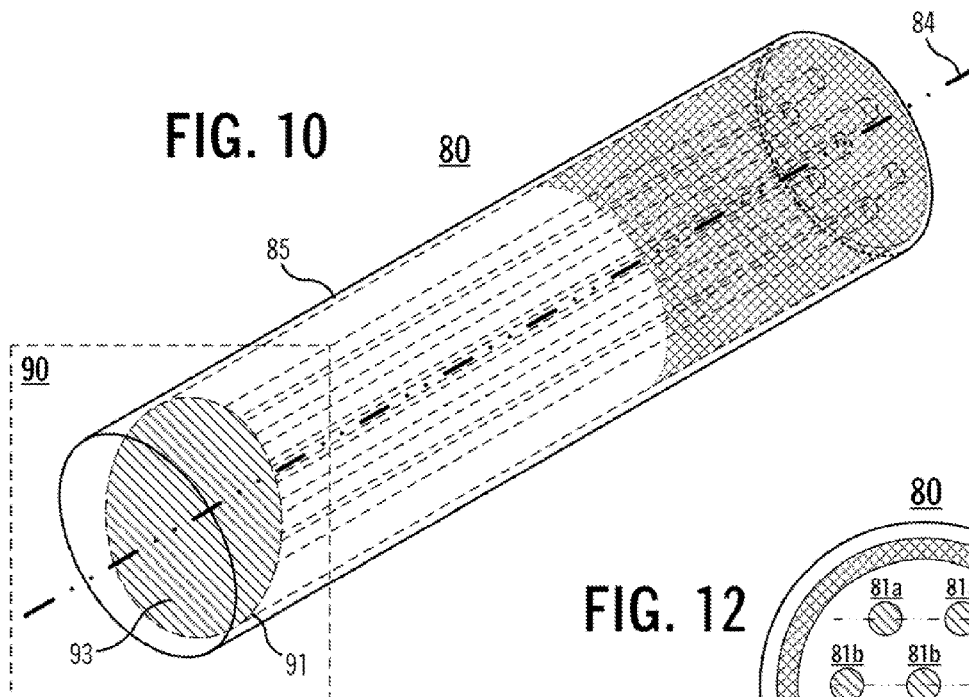
FIG. 10 shows an isometric view of the tip of a segment of a multicore fiber that has been provided with a low-backreflection termination structure in accordance with a further aspect of the present invention.
Figure 12:
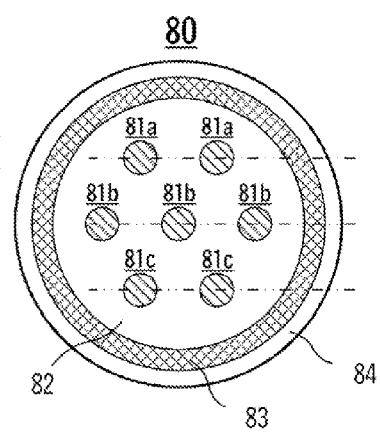
FIG. 12 shows a cross section view of the multicore fiber tip shown in FIGS. 10 and 11 through the plane 12-12.
Figure 11:
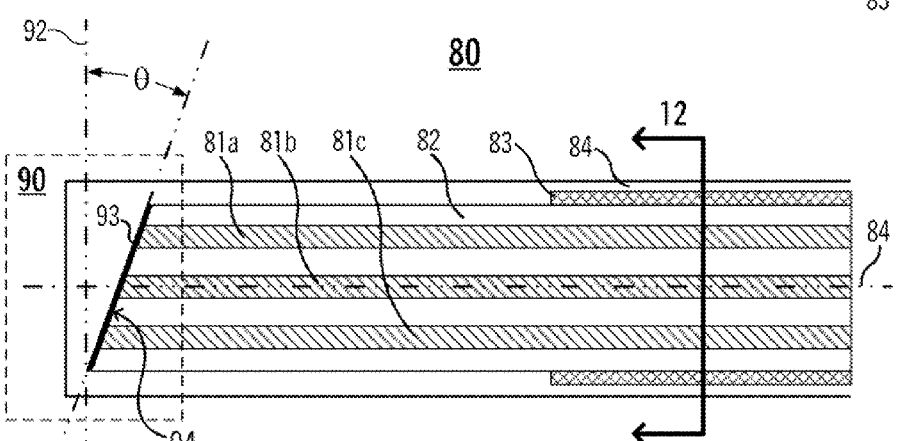
FIG. 11 shows a side cross section view of the multicore fiber tip and termination structure shown in FIG. 10.

FIG. 10 shows an isometric view of the tip of a segment of a multicore fiber (MCF) 80 that is provided with a low-backreflection termination structure 90 in accordance with the present invention. FIG. 11 shows a side cross section view of MCF 80, and FIG. 12 shows a cross section view of MCF 80 through the plane 12-12.

MCF 80 has seven cores, including a central core and six satellite cores arranged symmetrically around the central core. As shown in FIG. 12, in the present example, the seven MCF cores are arranged in three rows: a top row 81a; a middle row 81b; and a bottom row 81c. Multicore sensor fibers are typically employed in shape/position sensor applications. Single-core sensor fibers, such as fiber 40 discussed above, are typically employed in distributed temperature sensing applications, and the like.

MCF 80 has an endface 91 with an angle of θ with respect to a plane 92 perpendicular to the MCF axis 84. The MCF tip is coated with a suitable material 93, such as indium, gold, or chromium, or a suitable combination thereof, having a suitable adherence to silica and providing high reflectivity (i.e., ~100%). It would also be possible to use multilayer coatings of dielectric materials such as $TiO_2$ and $ZrO_2$, or other suitable material.

According to a further aspect of the invention, some or all of the exposed cylindrical surface of the glass cladding 82 at the fiber tip is coated with a suitable polymer 84. The added coating 84 protects the tip from mechanical damage and also help dissipate light that resides in the fiber cladding 82. As discussed above, the refractive index of the added coating 84 is taken into account in determining a suitable value for the endface angle θ, particularly if the refractive index of the coating 84 is lower than the refractive index of the cladding 82. According to a further aspect of the invention, the fiber tip is coated with a suitable material that absorbs light at the sensor's operating wavelength.

Figure 13:
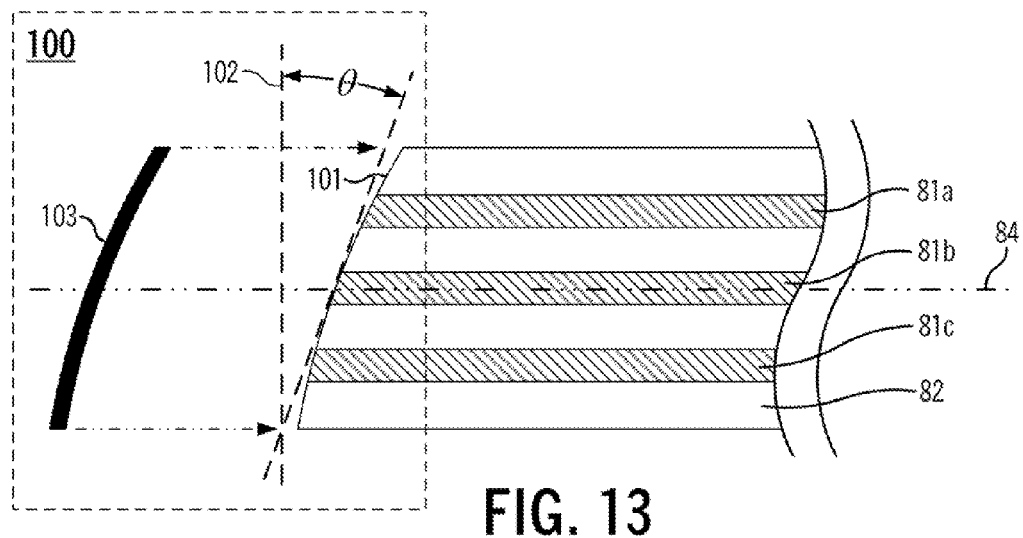
FIGS. 13 and 14 shows a closeup view of an alternative termination structure according to a further aspect of the invention for the multicore fiber tip shown in FIGS. 10 and 11.
Figure 14:
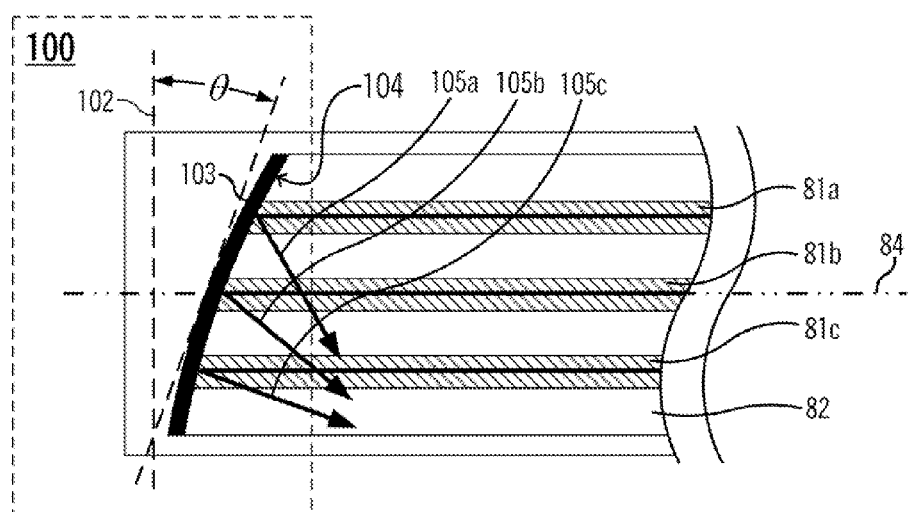

FIGS. 13 and 14 shows a closeup view of an alternative termination structure 100 for multicore fiber 80 according to a further aspect of the invention. In termination structure 100, the fiber endface is polished to have an angled convex shape. A suitable material is applied to the endface to create a reflective surface having a correspondingly convex shape.

The convexity of the reflective surface is configured to create different angles of reflection for different cores. As shown in FIG. 14, light traveling through a middle core 81b is backreflected at an angle of 2θ relative to the fiber axis 84; light traveling through an upper core 81a is backreflected at an angle greater than 2θ; light traveling through a lower core 81c is reflected at an angle less than 2θ. The precise shape of the endface is configured to achieve optimum suppression for light traveling in the different cores.

Figure 15:
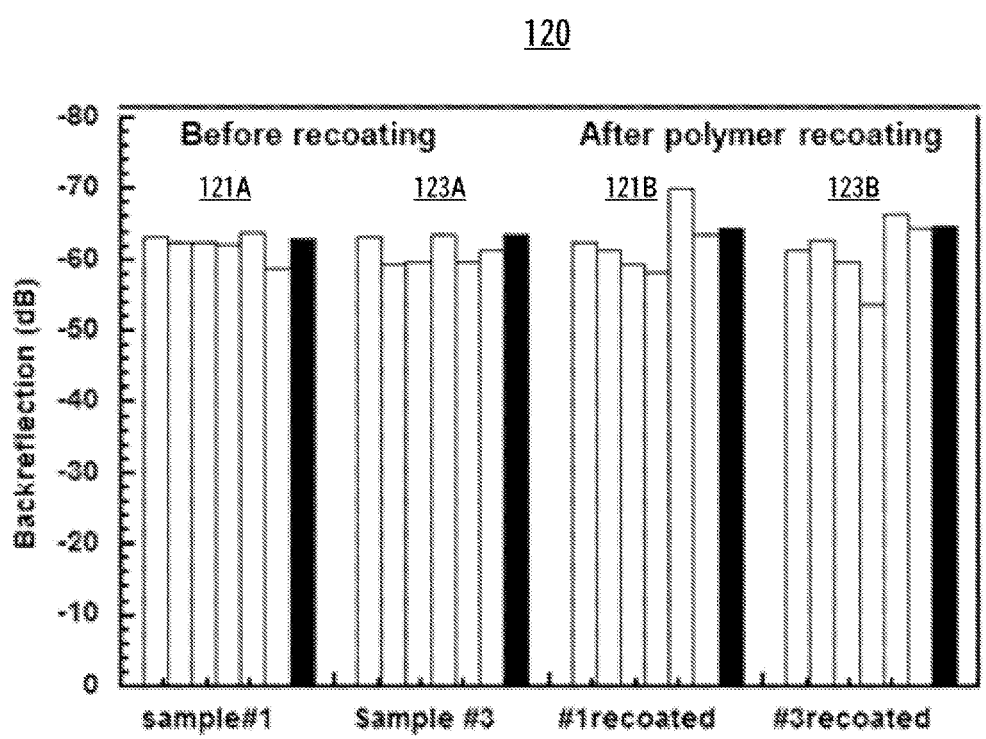
FIG. 15 shows a bar graph setting forth the measured backreflection for two samples of a seven-core sensor fiber terminated in accordance with the present invention.

FIG. 15 shows a bar graph 120 setting forth the measured backreflection for two samples (sample#1 and sample#3) of a seven-core sensor fiber terminated by polishing at 20-degree angle, and coated with an indium/gold coating. Bar groups 121A and 123B show the 7-core reflection measured for each of the two samples with metal coating, prior to polymer coating. Bar groups 121B and 123B show the same two samples subsequent to coating of the samples with a high-index polymer. As shown in FIG. 14, tip backreflection can be suppressed by ~−60 dB. The amount of suppression of tip backreflection is limited by the smoothness of the polishing and metal coating applied onto the polished endface.

General Technique

Figure 16:
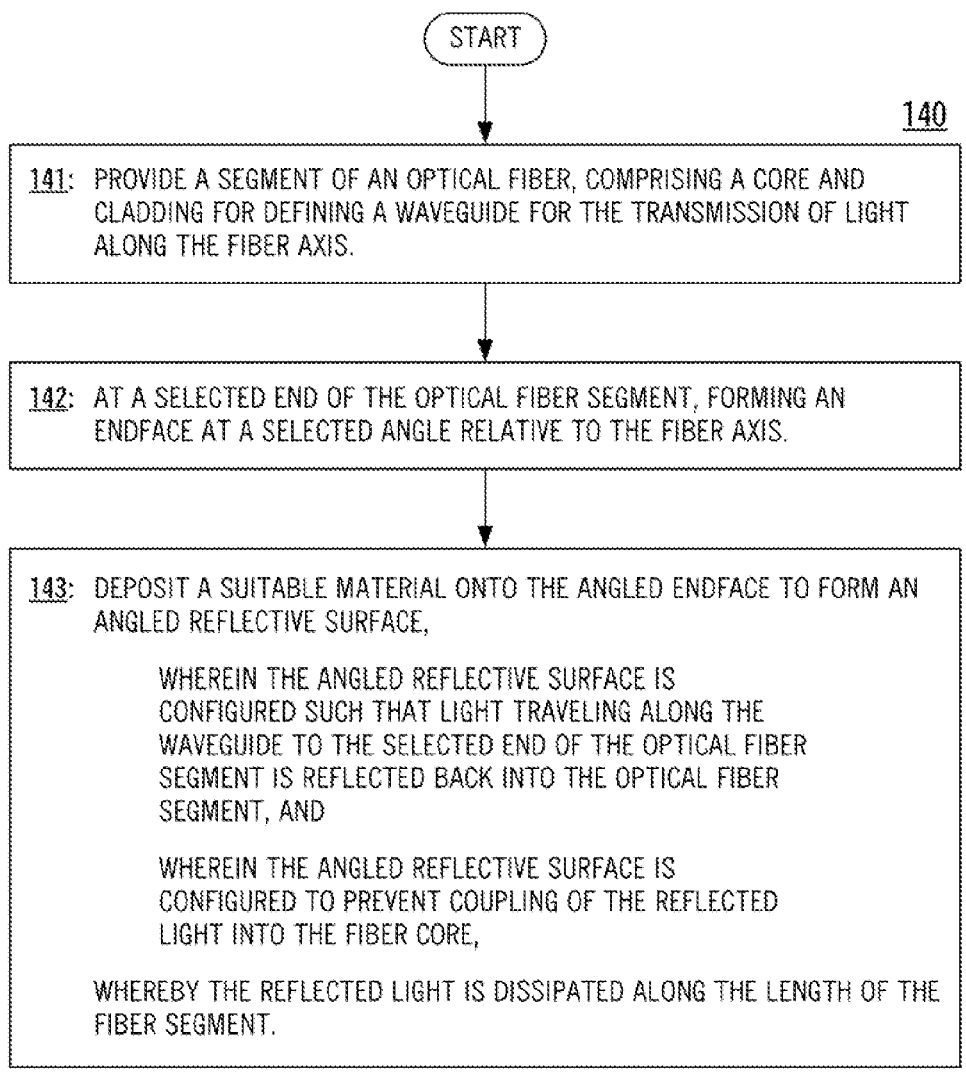
FIG. 16 shows a flowchart illustrating a general technique according to the invention.

FIG. 16 shows a flowchart illustrating a general technique 140 according to the above-described aspects of the invention, comprising the following steps:

Step 141: Provide a segment of an optical fiber, comprising a core and cladding for defining a waveguide for the transmission of light along the fiber axis Step 142: At a selected end of the optical fiber segment, form an endface at a selected angle relative to the fiber axis.

Step 143: Deposit a suitable material onto the angled endface to form an angled reflective surface,
wherein the angled reflective surface is configured such that light traveling along the waveguide to the selected end of the optical fiber segment is reflected back into the optical fiber segment, and
wherein the angled reflective surface is configured to prevent coupling of the reflected light into the fiber core,
whereby the reflected light is dissipated along the length of the fiber segment.

While the foregoing description includes details that will enable those skilled in the art to practice the invention, it should be recognized that the description is illustrative in nature and that many modifications and variations thereof will be apparent to those skilled in the art having the benefit of these teachings. It is accordingly intended that the invention herein be defined solely by the claims appended hereto and that the claims be interpreted as broadly as permitted by the prior art.

What is claimed is:

1. A method for terminating an optical fiber, comprising:
(a) providing a segment of an optical fiber, comprising a core and cladding for defining a waveguide for the transmission of light along the fiber axis;
(b) at a selected end of the optical fiber segment, forming an endface at a selected angle relative to the fiber axis; and
(c) depositing a reflective material onto the angled endface to form an angled reflective surface,
wherein the angled reflective surface is configured such that light propagating along the waveguide to the selected end of the optical fiber segment is reflected back into the optical fiber segment, and
wherein the angled reflective surface is configured to prevent coupling of the backreflected light into the fiber core,
thereby allowing the backreflected light to dissipate along the length of the fiber segment,
wherein the angled endface is configured to have an angle θ relative to the fiber axis, wherein light traveling along the waveguide towards the selected end of the optical fiber segment is reflected back into the optical fiber segment at an angle 2θ, and wherein a fraction of the reflected light is coupled into the fiber core in accordance with a relationship $$R = \frac{2}{1+\cos^2(2\theta)} \exp\left(-\frac{2\pi^2 n^2 \omega^2}{\lambda^2} \frac{2\sin^2(2\theta)}{1+\cos^2(2\theta)}\right),$$

where n is the core refractive index of the core, ω is the spot size, and λ is the wavelength of the transmitted light.

2. The method of claim 1, wherein the backreflected light dissipates in a coating surrounding the fiber cladding.

3. The method of claim 2, wherein the coating has a refractive index that is higher than that of the fiber cladding.

4. The method of claim 1, wherein the formed endface and the angled reflective surface are flat.

5. The method of claim 1,
wherein a polishing technique is used to create the angled endface.

6. The method of claim 1,
wherein a cleaving technique is used to create the angled endface.

7. The method of claim 1,
wherein the optical fiber segment comprises a cladding and a plurality of cores for defining a respective plurality of waveguides,
wherein the angled reflective surface is configured such that light traveling to the selected end of the optical fiber segment along one or more of the plurality of waveguides is reflected back into the optical fiber segment, and
wherein the angled reflective surface is configured to prevent coupling of the reflected light into any of the fiber cores.

8. The method of claim 7, wherein the formed endface and the angled reflective surface have a convex shape.

9. The method of claim 1, further including applying a protective outer coating over the angled reflective surface.

10. The method of claim 1,
wherein, in step (c), the reflective material is deposited onto the angled endface at a thickness of less than 10 micrometers.

11. The method of claim 10,
wherein step (c) comprises depositing a metal onto the angled endface.

12. The method of claim 1,
wherein step (c) comprises depositing a multilayer dielectric coating onto the angled endface.

13. A termination structure for an optical fiber having a core and a surrounding cladding, comprising:
an endface formed at the fiber tip having a selected angle relative to the fiber axis; and
a reflective material deposited onto the angled endface to form an angled reflective surface,
wherein the angled reflective surface is configured such that light propagating along the waveguide to the fiber tip is reflected back into the optical fiber, and wherein the angled reflective surface is configured to prevent coupling of the backreflected light into the fiber core,
thereby allowing the backreflected light to dissipate along the length of the fiber segment,
wherein the angled endface is configured to have an angle θ relative to the fiber axis, wherein light traveling along the waveguide towards the selected end of the optical fiber segment is reflected back into the optical fiber segment at an angle 2θ, and wherein a fraction of the reflected light is coupled into the fiber core in accordance with a relationship $$R = \frac{2}{1+\cos^2(2\theta)} \exp\left(-\frac{2\pi^2 n^2 \omega^2}{\lambda^2} \frac{2\sin^2(2\theta)}{1+\cos^2(2\theta)}\right),$$

where n is the core refractive index of the core, ω is the spot size, and λ is the wavelength of the transmitted light.

14. The optical fiber termination structure of claim 13, wherein the backreflected light dissipates in a coating surrounding the fiber cladding.

15. The optical fiber termination structure of claim 14, wherein the coating has a refractive index that is higher than that of the fiber cladding.

16. The optical fiber termination structure of claim 13, wherein the formed endface and the angled reflective surface are flat.

17. The optical fiber termination structure of claim 13,
wherein the optical fiber segment comprises a cladding and a plurality of cores for defining a respective plurality of waveguides,
wherein the angled reflective surface is configured such that light traveling to the selected end of the optical fiber segment along one or more of the plurality of waveguides is reflected back into the optical fiber segment, and
wherein the angled reflective surface is configured to prevent coupling of the reflected light into any of the fiber cores.

18. The optical fiber termination structure of claim 17, wherein the formed endface and the angled reflective surface have a convex shape.

19. The optical fiber termination structure of claim 13, further including a protective outer coating over the angled reflective surface.

20. The optical fiber termination structure of claim 13, wherein the reflective material comprises a metal.

21. The optical fiber termination structure of claim 13, wherein the reflective material comprising a multilayer dielectric coating onto the angled endface.

* * * * *